(12) United States Patent
Yanni et al.

(10) Patent No.: US 12,268,663 B2
(45) Date of Patent: Apr. 8, 2025

(54) METHOD FOR TREATING PRURITUS

(71) Applicant: Pruvyc Pharma, LLC, Cary, NC (US)

(72) Inventors: John M. Yanni, Burleson, TX (US); Eric C. Carlson, Burleson, TX (US)

(73) Assignee: PRUVYC PHARMA, LLC, Cary, NC (US)

( * ) Notice: Subject to any disclaimer, the term of this patent is extended or adjusted under 35 U.S.C. 154(b) by 0 days.

(21) Appl. No.: 17/470,243

(22) Filed: Sep. 9, 2021

(65) Prior Publication Data
US 2023/0085380 A1 Mar. 16, 2023
US 2023/0210809 A9 Jul. 6, 2023

Related U.S. Application Data

(60) Provisional application No. 63/087,212, filed on Oct. 3, 2020.

(51) Int. Cl.
| | | |
|---|---|---|
| *A61K 31/335* | (2006.01) | |
| *A61K 9/00* | (2006.01) | |
| *A61K 9/06* | (2006.01) | |
| *A61K 47/02* | (2006.01) | |
| *A61K 47/06* | (2006.01) | |
| *A61K 47/08* | (2006.01) | |
| *A61K 47/10* | (2017.01) | |
| *A61K 47/14* | (2017.01) | |
| *A61K 47/18* | (2017.01) | |
| *A61K 47/24* | (2006.01) | |
| *A61K 47/32* | (2006.01) | |
| *A61K 47/44* | (2017.01) | |

(52) U.S. Cl.
CPC .......... *A61K 31/335* (2013.01); *A61K 9/0014* (2013.01); *A61K 9/06* (2013.01); *A61K 47/02* (2013.01); *A61K 47/06* (2013.01); *A61K 47/08* (2013.01); *A61K 47/10* (2013.01); *A61K 47/14* (2013.01); *A61K 47/183* (2013.01); *A61K 47/24* (2013.01); *A61K 47/32* (2013.01); *A61K 47/44* (2013.01)

(58) Field of Classification Search
CPC ...................................................... A61K 9/06
See application file for complete search history.

(56) References Cited

U.S. PATENT DOCUMENTS

| | | | | |
|---|---|---|---|---|
| 6,506,375 | B1 * | 1/2003 | Barr | ................. A61Q 5/12 424/59 |
| 2015/0290151 | A1 * | 10/2015 | Birbara | .............. A61K 31/00 514/625 |
| 2018/0015166 | A1 * | 1/2018 | Schmitt | ............. A61K 31/55 |

OTHER PUBLICATIONS

Olopatadine Hydrochloride Improves Dermatitis Score and Inhibits Scratch Behavior in NC/Nga Mice Murota et al. Int Arch Allergy Immunol 2010; 153:121-132 (Year: 2010).*
Olopatadine/Mometasone Combination Nasal Spray for the Treatment of Seasonal Allergic Rhinitis: A Pooled Analysis of Efficacy and Safety Gross et al. J Allergy Clin Immunol, vol. 143, 2019 (Year: 2019).*
Patanase Drug Label Information NIH U.S. National Library of Medicine (Year: 2012).*
https://www.lovelyskin.com/o/fixmyskin-healing-body-balm-unscented-with-1-hydrocortisone LovelySkin Inc. (Year: 2019).*
https://www.benadryl.ca/products/benadryl-itch-cream Johnson & Johnson Inc. (Year: 2019).*
Pruritus: an overview. What drives people to scratch an itch? Lavery et al. Ulster Med J 2016;85(3):164-173 (Year: 2016).*
Healing with Zinc Oxide—A Guide to the Use of Paste Bandages Evolan Pharma AB https://youtu.be/9IMxaXHbsfY Feb. 29, 2020 (Year: 2020).*
Effect of topical cromoglycate solution on atopic dermatitis Kimata et al. Eur J Pediatr (1994) 153 : 66-71 (Year: 1994).*
Olopatadine eye drops are effective topical treatment for cutaneous mastocytomas: A novel treatment Singh et al. Dermatologic Therapy. 2020;33:e14045. (Year: 2020).*
Olopatadine-mometasone combination nasal spray: Evaluation of efficacy and safety in patients with seasonal allergic rhinitis Hampel et al. Allergy and Asthma Proceedings Jul. 2019, vol. 40, No. 4 (Year: 2019).*
Elocon FDA Label Revision May 2018 (Year: 2018).*

* cited by examiner

*Primary Examiner* — Jeffrey S Lundgren
*Assistant Examiner* — Eric Tran
(74) *Attorney, Agent, or Firm* — Patterson + Sheridan, LLP

(57) ABSTRACT

Methods for treating pruritis in humans and animals using topically administrable compositions containing olopatadine are disclosed. The compositions quickly relieve itchy skin.

13 Claims, No Drawings

METHOD FOR TREATING PRURITUS

The present invention relates to a method of treating itchy skin in humans and animals. In particular, the present invention is directed towards the use of topically administered compositions containing olopatadine to quickly relieve itchy skin.

BACKGROUND OF THE INVENTION

Pruritus or itch is a sensation of the skin that stimulates a human or animal to scratch, which can have a wide variety of etiologies including underlying medical conditions. Common examples of causes beyond underlying medical conditions are insect bites, dryness of the epidermis, healing wounds, infections, mechanical irritation, burns or synthetic and natural chemical exposure such as exposure to members of the Anacardiaceae family of plants (e.g. poison ivy and poison oak).

Olopatadine is a known anti-allergic agent useful for treating allergic conditions. Topically applied olopatadine is commercially available for administration to the ocular surface for the treatment of allergic conjunctivitis and a nasal spray is commercially available for the treatment of allergic rhinitis. Additionally, systemic olopatadine administered via an oral tabled is commercially available in Japan for the treatment of allergic disease. Olopatadine has been shown to bind both the histamine H1 and serotonin S2 receptors. It also inhibits allergic mediator release from connective tissue mast cells. These connective tissue mast cells are the type that predominate in human skin. The pharmacological profile of olopatadine permits use of the drug to prevent an allergic response from occurring (mast cell stabilization) and inhibitis the effect of the released pro-inflammatory mediators on tissue receptors providing therapeutic benefits.

Clinical studies utilizing topical ocular administration of olopatadine have demonstrated a significant inhibition of itching, tearing, photophobia and hyperemia (redness) that are a result of the allergic response (Sarker et. al. *Therapy* (2011) 8(5), 545-553). The relief and cessation of these clinical signs and symptoms are related to the pharmacological activities of olopatadine through inhibition of the histamine pathway and pro-inflammatory mediators.

A host of treatments for itchy skin are currently available, including topical antihistamines, corticosteroids and transient analgesics. Nevertheless, a significant unmet medical need remains for a safe, rapidly effective, durable treatment that is easily applied to the affected area of the skin.

SUMMARY OF THE INVENTION

The present invention provides topically administrable dermatological compositions for treating pruritus. The compositions contain olopatadine and are safe and easy to apply to the epidermis of the skin. The present invention also relates to a method of treating pruritus by topically administering these olopatadine compositions in a formulation and delivery mechanism that provides localized, fast and durable relief.

DETAILED DESCRIPTION OF THE INVENTION

The compositions of the present invention are topically administrable and dermatologically acceptable. They contain olopatadine, preferably as olopatadine hydrochloride, as an active ingredient. The compositions comprise olopatadine in an amount from 0.1 to 1% (w/w), preferably 0.2-0.7% (w/w) (and if the compositions contain a salt form of olopatadine, such as olopatadine hydrochloride, then the compositions should contain an amount of the salt form such that they contain an equivalent amount of olopatadine). As used herein, 'olopatadine' refers to olopatadine or an equivalent amount of a salt of olopatadine. As known in the art, it may be necessary to use solubilization or stabilization aids, such as polymers like polyvinypyrrolidone, to obtain stable solution compositions comprising olopatadine hydrochloride at concentrations of 0.2% and higher (see, for example, U.S. Pat. Nos. 6,995,186 and 8,791,154). Additionally, the compositions comprise dermatologically acceptable excipients known in the art, such as surfactants, lubricating or moisturizing agents, buffering agents, penetration enhancers, etc. For example, excipients are selected such that the formulation is non-irritating and does not alter membrane integrity and skin functionality. Ingredients that have skin integrity restoring, replenishing and collagen synthesis abilities include sphingolipids, ceramides, tri and tetrapeptides etc. Excipients that provide slip, glossy and smooth feel to the formulations include dimethicones, alkyl benzoates, neopentanoates, distearates etc. Emollients are the excipients that can soothe and soften the skin and include, isopropyl palmitate, lanolin alcohol, diethyl sebacate, and isostearyl isostearate etc. Humectants can retain the moisture and elevate the hydration of skin, and include, glycerin, ethylhexylglycerin, butylene glycol, acteamides and other glycols. Formulations may also include antioxidants such as squalane, ascorbic acid, hydrolyzed collagen, gluconates, and vitamin E etc. Anti-microbials and preservatives include potassium sorbate, DMDM hydantoin, chlorphenesin etc. As olopatadine is a hydrophobic drug, non-ionic surfactants such as polysorbates, sorbitans, palmates, lactylates etc. are included in the formulation to enhance the solubility of the drug substance. Other solubility enhancers include polyvinylpyrrolidone, cylcodextrins caprylates etc. In one embodiment, the compositions comprise shampoo ingredients and are formulated as a shampoo. The compositions preferably have a pH of 3 to 8. In one embodiment, the compositions have a pH of 6.5 to 7.5. In another embodiment, because olopatadine may crystallize at higher pH's (e.g., 6.5 to 7), the pH of the formulation may be maintained at ~4 by using either HCl or buffers such as sodium dihydrogen phosphate to adjust the pH. In another embodiment, the delivery vehicle for olopatadine is non-aqueous and formulated in a petroleum-based ointment or erodible or non-erodible patch, such as an erodible patch comprising polylactic acid or similar polymer.

In one embodiment, the compositions of the present invention may include a second active ingredient, such as an anti-inflammatory drug or antimicrobial agent. In another embodiment, the compositions contain an insecticide. In a further embodiment, the compositions contain an insect repellant, such as DEET.

The compositions of the present invention are formulated as dosage forms suitable for application to the skin, such as lotions, gels, foams, semi-solids or solids. The compositions can be packaged in containers that make applying the compositions to the skin easy and efficient. An example of such dosage forms and packages include a solution packaged in a spray bottle (such as a bottle with a pump spray top or propellant). In another embodiment, the compositions are a solution (lotion) packaged in a bottle containing a rollerball applicator (roller bottle). In still another embodiment, the compositions are a gel, semi-solid or wax in a tube or container having a mechanism for advancing the product to the tip of the container (such as used for lip-balm or stick deodorant). In yet another embodiment, the compositions of the present invention are a gel, ointment or cream packaged in a squeezable container. In another embodiment, the compositions of the present invention are formulated as a soap or shampoo. In another embodiment the compositions of the present invention are formulated within or on the surface of an erodible or non-erodible patch or adhesive bandage to significantly increase residence and exposure time durations.

EXAMPLES

Representative topically administrable dermatological compositions according to the present invention are shown in Tables 1-31 below.

TABLE 1

Topical roll-on gel

| Ingredients | Functionality | Topical IID Limits | % w/w |
|---|---|---|---|
| Olopatadine HCl | Active | Up to 1% | 0.2, 0.7, or 1 |
| Povidone | Thickening agent, binder | 4% | 1 |
| Hydroxy propylcellulose | Thickening agent, binder | 4% | 1 |
| Glycerin | Humectant | 60% | 10 |
| Benzalkonium Chloride | Preservative | 0.75% | 0.5 |
| NaoH/HCl | pH adj | pH adj | q.s. |
| Transcutol-P | Penetration enhancer | — | 10 |
| Edetate diSodium | Chelating agent | 1 | 0.01 |
| Water | Diluent | N/A | q.s. to 100 |

TABLE 2

Topical roll-on gel

| Ingredients | Functionality | Topical IID Limits | % w/w |
|---|---|---|---|
| Olopatadine HCl | Active | Up to 1% | 0.2, 0.7, or 1 |
| Carbomer (Type C) | Thickening agent, binder | 4% | 1 |
| Propylene glycol | Permeation enhancer | 99% | 10 |
| Glycerin | Humectant | 60% | 5 |
| Benzyl alcohol | Preservative | 2.7% | 1 |
| NaoH/HCl | pH adj | pH adj | q.s. |
| Edetate diSodium | Chelating agent | 1 | 0.01 |
| Water | Diluent | N/A | q.s. to 100 |

TABLE 3

Topical roll-on emulsion gel

| Ingredients | Functionality | Topical IID Limits | % w/w |
|---|---|---|---|
| Olopatadine HCl | Active | Up to 1% | 0.2, 0.7, or 1 |
| Carbomer (Type C) | Thickening agent, binder | 4% | 1 |
| Propylene glycol | Permeation enhancer | 99% | 10 |
| Mineral oil | Oil/Emollient | 70% | 20 |
| Tween 80 | Surfactant | 12% | 6 |

TABLE 3-continued

Topical roll-on emulsion gel

| Ingredients | Functionality | Topical IID Limits | % w/w |
|---|---|---|---|
| Glyceryl monostearate | Emulsifier | 8% | 4 |
| Glycerin | Humectant | 60% | 5 |
| Sorbic acid | Preservative | 2% | 0.5 |
| NaoH/HCl | pH adj | pH adj | q.s. |
| Edetate diSodium | Chelating agent | 1% | 0.01 |
| Water | Diluent | N/A | q.s. to 100 |

TABLE 4

Topical roll-on gel

| Ingredient | Functionality | Topical IID Limits | % w/w |
|---|---|---|---|
| Olopatadine HCl | Active | Up to 1% | 0.2, 0.7, or 1 |
| Tyloxapol | Non-ionic surfactant | 0.10% | 0.1 |
| Tween 80 | Non-ionic surfactant | 15% | 2 |
| Povidone | Vehicle/Solvent | — | 1 |
| Dibasic sodium phosphate | pH adj | — | 0.5 |
| Propylene glycol | Viscosifying agent/Solvent | 99.98% | 10 |
| PEG 400 | Viscosifying agent/Solvent | 99% | 10 |
| Hypromellose | Thickening agent, binder | 4% | 1 |
| Sorbic acid | Preservative | 0.75% | 0.5 |
| HCl/NaOH | pH adj | pH adj | q.s. |
| Ethanol | Penetration enhancer | — | 10 |
| EDTA | Chelating agent | 1 | 0.01 |
| Water | Diluent | — | q.s. to 100 |

TABLE 5

Topical roll-on emollient cream

| Material | % w/w | Functionality |
|---|---|---|
| Olopatadine | 0.2, 0.7. or 1 | Active |
| Decyl Cocoate | 3 | skin-conditioning agent - occlusive, emollient |
| Octyl dodecanol | 2 | emollient and emulsifier |
| Stearyl heptanoate | 2 | emollient |
| Myristyl myristate | 0.5 | Moisture, texture, stabilizer |
| Menthyl lactate | 1 | cooling or flavoring agent |
| Cetearyl glucoside | 1 | emulsifying, and surfactant |
| Tetrapeptide-21 | 1.5 | superior collagen, hyaluronic acid and fibronectin |
| Glycerin | 3 | Humectant |
| Butylene glycol | 5 | Humectant, solvent, and emollient |
| Carbomer 980 | 0.2 | Gelling agent |
| Pentylene glycol | 5 | skin conditioning |
| Sodium hyaluronate | 0.1 | lubricant, thickening agent |
| Polyglyceryl-4 Diisostearate/ Polyhydroxystearate/ Sebacate | 0.4 | emulsifying, surfactant/cleansing, emulsion stabilizing |
| Tween 80 | 2 | non-ionic surfactant |
| Sodium Isostearate | 0.2 | non-ionic surfactant |
| Diisopropyl adipate | 5 | Lubricant |
| Ethylhexyl stearate | 0.4 | skin-conditioning agent - emollient and emollient |
| Tyloxapol | 0.1 | non-ionic surfactant |
| Purified Water | q.s. to 100 | Diluent |

TABLE 6

Topical roll-on emollient cream

| Excipient | % w/w | Property |
|---|---|---|
| Olopatadine | 0.2, 0.7, or 1 | Active |
| Diethylhexyl carbonate | 2 | Unique emollient especially suitable for light and non-oily skin care and sun care products. Oil with low viscosity, high spreading properties and good solvency for crystalline actives. |
| Bis-Peg/Ppf-14/14 Dimethicone | 5 | Skin-conditioning agents, emollients, surfactants, emulsifying agent |
| Isopropyl palmitate | 7 | Light emollient with medium spreading properties and high refatting characteristics. Good solubilizer for oil-soluble active ingredients. Shows very good wetting properties of hydrophobically coated pigments. |
| Caprylyl glycol | 5 | humectant, preservative |
| Palmitoyl Tetrapeptide-7 | 0.5 | regenerating peptide |
| Panthenol | 0.5 | moisturizer |
| Dipotassium Glycyrrhizate | 5 | skin-conditioning ingredient |
| Polyglyceryl-6 Behenate | 2 | Emulsifier |
| Hypromellose | 1 | Gelling agent |
| Sodium Anisate | 0.5 | preservative |
| Polyisobutylene | 3 | Glossing agent, stabilizer, film former to enhance the water resistance of O/W products. |
| Sorbitan Laurate | 1 | surfactant - emulsifying agent and emulsifying |
| Sorbitan monopalmitate | 2 | surfactant - emulsifying agent |
| Lanolin Alcohol | 2 | emollient, skin replenishing |
| Methylglucose Isostearate | 2 | Sugar-based, nonionic co-emulsifier for W/O creams with moisturizing properties. |
| Jojoba Oil | 5 | Emollient that softens and smooth the skin |
| 3-o-Ethyl Ascorbic Acid | 0.5 | antioxidant, skin brightening |
| Water | q.s. to 100 | Diluent |
| HCl | pH 5-6 | pH Adj |

TABLE 7

Topical roll-on lotion

| Excipient | % w/w | Property |
|---|---|---|
| Olopatadine | 0.2, 0.7, or 1 | Active |
| Stearyl Dimethicone | 5 | opacity and a silky feel to cosmetic products |
| Methoxy PEG/PPG-25/4 Dimethicone | 5 | Emulsifying, Emulsion Stabilising |
| Myristyl Myristate | 5 | improve the texture of formulations and help to keep the skin moisturized and hydrated. Myristyl myristate is generally used as an emollient, texture enhancer, and co-emulsifier. |
| Diethylhexyl Carbonate | 3 | Unique emollient especially suitable for light and non-oily skin care and sun care products. It is an oil with low viscosity, high spreading properties and good solvency for crystalline actives. |
| Glycine | 0.1 | improve moisture retention, increase collagen production, and promote skin repair and regeneration |
| Glycosphingolipids | 0.1 | Skin-Restoring, Skin-Replenishing |
| Arginine | 0.1 | protect the skin from free radicals, increase the skin's visible hydration levels, and potentially support collagen production. |
| Isopropyl Palmitate | 5 | Light emollient with medium spreading properties and high refatting characteristics. Good solubilizer for oil-soluble active ingredients. Shows very good wetting properties of hydrophobically coated pigments. |

TABLE 7-continued

Topical roll-on lotion

| Excipient | % w/w | Property |
| --- | --- | --- |
| Beta-Cyclodextrin | 2 | Olopatadine solubilizing agent |
| 1-Methylhydantoin-2-Imide | 0.5 | Skin conditioner, skin brightening, pH regulating |
| Glycol Distearate | 1 | Pearlizing agent. Bright white pearlizing effect. |
| Methyl Glucose Sesquistearate | 2 | PEG-free emulsifier for cosmetic O/W creams and lotions. Stable emulsions at pH 3.5-8.5. Good compatibility with active ingredients and electrolytes. |
| C12-15 Alkyl Benzoate | 5 | excellent solvent properties for lipophilic active ingredients and UV filters. Especially suitable for sun care formulations and skin care products. Leaves a pleasant, but non-oily skin feel. |
| Isostearyl Isostearate | 5 | emolliency and luxurious softness on skin |
| Aloevera Juice Extract | 5 | anti-inflammatory, anti-oxidant |
| a-Tocopherol | 0.5 | anti-oxidant |
| Potassium sorbate | 0.1 | antimicrobial and antifungal properties |
| Xanthan Gum | 0.2 | Gelling agent |
| HCl | pH 4 | pH Adj |
| Water | q.s. to 100 | Diluent |

TABLE 8

Topical roll-on emollient cream

| Excipient | % w/w | Property |
| --- | --- | --- |
| Olopatadine | 0.2, 0.7. or 1 | Active |
| Palmitoyl Oligopeptide | 0.5 | skin-restoring ability |
| Ethylhexylglycerin | 5 | emollient and humectant |
| Caprooyl Tetrapeptide-3 | 0.5 | Skin-Restoring |
| Bis-PEG/PPG-14/14 Dimethicone | 5 | skin-conditioning agent - emollient, surfactant |
| Squalane, | 5 | moisturizing; oil-soluble antioxidant. |
| Butylene Glycol | 10 | skin-conditioning agent - miscellaneous, solvent, viscosity decreasing agent, humectant, |
| C12-15 Alkyl Benzoate | 2 | Emollient, texture enhancer, anti-microbial |
| Diethyl sebacate | 2 | Emollient, skin conditioning, solvent |
| Isopropyl Isostearate | 5 | highly emollient ester; It imparts good spreadability and slip in various formulation types. |
| Glyceryl Caprylate, | 2 | co-emulsifier that is mainly used to stabilize O/W- emulsions |
| Dmdm Hydantoin | 0.5 | preservative, antimicrobial agent |
| PEG-200 Hydrogenated Glyceryl Palmate | 2 | surfactant - solubilizing agent, cleansing, emulsifying, and solvent |
| Sodium Lauroyl Lactylate | 2 | surfactant, emulsifier, and moisturizer. |
| Polyglyceryl-4 Caprate | 5 | solubilizer, emulsifier |
| Polyvinylpyrrolidone | 5 | Film forming agent |
| Polyvinyl alcohol (1%) | 10 | Solubilizing agent, surfactant |
| Hydrolyzed collagen | 0.5 | Antioxidant |
| Hydroxyethyl cellulose | 1 | Gelling agent |
| Chlorphenesin, | 0.5 | synthetic preservative |
| HCl | pH 4 | pH Adj |
| Lavendar Oil | 2 | anti-inflammatory that can reduce redness and a natural hydrator that can repair dry skin without making it too greasy. |
| Water | q.s. to 100 | Diluent |

TABLE 9

Topical roll-on emollient cream

| Excipient | % w/w | Property |
|---|---|---|
| Olopatadine | 0.2, 0.7. or 1 | Active |
| Pentaerythrityl Tetraethylhexanoate | 5 | emollient, binder, skin conditioning agent, and viscosity increasing agent |
| Ceramide EOP | 0.5 | crucial role in the skin barrier, |
| Phytosphingosine | 0.5 | crucial role in the skin barrier, |
| Sodium Hyaluronate | 0.2 | restore the skin's moisture, promoting a more revitalized and youthful complexion. |
| Copper Gluconate | 1 | Anti-oxidant |
| Palmitoyl Pentapeptide-4 | 0.5 | Skin-Restoring |
| cetyl PEG/PPG-10/1-dimethicone | 5 | Texture Enhancer, Silicones |
| Dioctyl sebacate | 5 | Emollient |
| Chlorphenesin | 0.5 | synthetic preservative |
| Panthenol | 0.5 | moisturizer |
| N-Propyl Palmitoyl Tripeptide-56 Acetate | 0.5 | moisturizers and support collagen production |
| Hydroxypropyl cellulose | 1 | Gelling agent |
| Nordihydroguaiaretic Acid | 0.5 | antioxidant |
| Dibasic sodium phosphate | pH 4 | pH Adj |
| Myristyl Myristate | 5 | improve the texture of formulations and help to keep the skin moisturized and hydrated. Myristyl myristate is generally used as an emollient, texture enhancer, and co-emulsifier. |
| Juniperus Communis Fruit Extract | 5 | Skin conditioning |
| Acetamide MEA | 5 | Humectant, skin conditioning agent |
| Chamomile Oil | 5 | increasing moisture and reducing inflammation. |
| Water | q.s. to 100 | Diluent |

TABLE 10

Topical cream

| MATERIAL | % w/w | FUNCTIONALITY |
|---|---|---|
| Olopatadine | 0.2, 0.7. or 1 | Active |
| Glycerin | 5 | Humectant |
| Niacinamide | 0.1 | replenish moisture to your skin barrier by decreasing TEWL |
| Butylene Glycol | 5 | Humectant, solvent, and emollient |
| Calendula Officinalis Extract | 1 | antifungal, anti-inflammatory, and antibacterial properties |
| Isostearyl Isostearate | 2 | Naturally-derived, medium emollient ester that imparts luxurious softness, slip agent |
| Propylene carbonate | 5 | solvent, viscosity decreasing agent, and viscosity controlling |
| Isohexadecane | 2 | solvent, cleansing agent, skin-conditioning agent, and a texture enhancer |
| Dimethiconol | 2 | skin conditioner, anti-foaming agent and emollient. |
| PEG-100 Stearate | 2 | High HLB co-emulsifier (with GMS) for O/W systems. |
| GMS Type II | 5 | consistency factors and co-emulsifiers; will help to enhance the viscosity with building up a liquid crystalline network in the water-phase (lamellar structure). |
| DMDM Hydantoin | 0.5 | preservative, antimicrobial agent |
| C13-14 Isoparaffin | 2 | emollient, thickening agent, and gelling ingredient |
| Palmitoyl Tetrapeptide-7 | 0.5 | Synthetic peptide to skin inflammation and the accompanying skin damage. |
| Hydrogenated Polydecene | 1 | fragrance ingredient, hair conditioning agent, skin-conditioning agent - emollient; skin-conditioning agent - miscellaneous, solvent, and emollient |

TABLE 10-continued

Topical cream

| MATERIAL | % w/w | FUNCTIONALITY |
| --- | --- | --- |
| Cetearyl Alcohol | 3 | soften the skin and thicken and stabilize topical products |
| Stearic Acid | 2 | Thickeners/Emulsifiers, Emollients, Skin-Replenishing |
| Sodium dehydroacetate | 0.5 | preservative |
| Chlorhexidine Digluconate | 0.5 | Antimicrobial |
| Schinziophyton Rautanenii Kernel Oil | 2 | emollient |
| Diethyl sebacate | 5 | Moisturizing agent, emollient, solvent, masking agent |
| Ascorbyl Glucoside | 0.2 | Antioxidant |
| Dibasic sodium phosphate | pH adj | pH Adjusting agent |
| Water | q.s. to 100 | Diluent |

TABLE 11

Topical cream

| MATERIAL | % w/w | FUNCTIONALITY |
| --- | --- | --- |
| Olopatadine | 0.2, 0.7. or 1 | Active |
| PEG-40 Stearate | 2 | Solubilizing agent, surfactant |
| Polyglyceryl-6 Distearate | 1 | skin-conditioning agent - emollient, surfactant - emulsifying agent, |
| Lauryl PEG-9 Polydimethylsiloxyethyl Dimethicone | 5 | act as silky moisturizers, conditioners, solvents, and delivery agents for other skin care ingredients. Silicones are able to help with skin redness and irritation due to their low surface tension, which enables them to spread easily across the surface of skin and form a protective covering. |
| Acrylic Acid/VP Crosspolymer | 0.5 | multi-functional rheology modifier, emulsion stabilization, reduces tack, and improves aethetics of hydroalcoholic sprays, and enhances skin feel properites. |
| Glycyrrhetinic Acid | 2 | Antioxidants, Skin-Soothing |
| Trehalose | 0.5 | moisturizer, skin protectant, and antioxidant |
| Acetyl Tetrapeptide-5 | 0.5 | Skin conditioning |
| C12-15 Alkyl Benzoate | 5 | emollient and texture enhancing agent, lightly conditioning, silky finish to products, excellent solvent properties for lipophilic active ingredients |
| Sodium hyaluronate | 0.1 | humectant, thickening agent |
| Diisopropyl Dimer Dilinoleate | 2 | Non-oily, heavy emollient ester that is rich and cushiony, slip agent |
| Pentylene Glycol | 5 | solvent and skin conditioning |
| Lecithin | 0.5 | thickener, stabilizer, and preservative, |
| Tocopherol | 0.5 | antioxidants |
| Cetyl Alcohol | 2.5 | emollient, thckening and stabilizing agent |
| Beeswax | 5 | anti-bacterial affects and can help heal minor skin irritations, moisturizer, vit A, thickener |
| Aluminum starch octenyl succinate | 1 | absorbent, anticaking agent, viscosity increasing agent - nonaqueous, anticaking, and viscosity controlling |
| Caprylyl Glycol, | 5 | humectant |
| Isohexadecane | 3 | Emollient |
| *PRUNUS ARMENIACA* KERNEL OIL/APRICOT KERNEL OIL | 5 | Highly moisturizing, emollient, Reduces inflammation, Antioxidants prevent free radical damage |
| Potassium sorbate | 0.1 | Preservative |
| Sodium Benzoate | 0.1 | corrosion inhibitor, fragrance ingredient, and preservative |
| Bis-Peg/Ppf-14/14 Dimethicone | 2 | Skin-conditioning agents; emollients; surfactant; emulsifying agent |
| PEG-200 Hydrogenated Glyceryl Palmate | 3 | surfactant - solubilizing agent, cleansing, emulsifying, and solvent |
| Glycol Stearate | 1 | emulsion stabilizer, opacifying agent, skin-conditioning agent - emollient, emollient, emulsifying, opacifying, and surfactant |
| HCl | pH Adj | pH adjusting agent |
| Water | q.s. to 100 | Diluent |

TABLE 12

Topical cream

| MATERIAL | % w/w | FUNCTIONALITY |
| --- | --- | --- |
| Olopatadine | 0.2, 0.7. or 1 | Active |
| Beta-Cyclodextrin | 2 | Solubilizer for olopatadine |
| Polyvinylpyrrolidone | 1 | Texture Enhancer, solvent |
| Glycol Distearate | 1 | Pearlizing agent. Bright white pearlizing effect. |
| Nylon-12 | 2 | Texture Enhancer, Absorbent |
| Dimethicone PEG-7 Cocoate | 5 | Silicone conditioning without greasiness or build-up |
| PPG-11 Stearyl Ether | 3 | Very high polar cosmetic emollient with a pleasant skin feel. Excellent solvent for lipophilic active ingredients and perfume oils. |
| Cetearyl Isononanoate | 3 | Cosmetic oil which forms a pleasant emollient film on the skin. Good solvent for active ingredients. Stable to oxidation. |
| PEG-30 Glyceryl Stearate | 1 | Solubilizer. Emulsifier for O/W creams and lotions. |
| Methyl Glucose Sesquistearate | 2 | PEG-free emulsifier for cosmetic O/W creams and lotions. Stable emulsions at pH 3.5-8.5. Good compatibility with active ingredients and electrolytes. |
| Methylpropanediol | 5 | hydrating the skin, leaving the skin looking hydrated, dewy, and smooth |
| Disodium PEG-5 Laurylcitrate Sulfosuccinate | 2 | surfactant - emulsifying agent, surfactant - hydrotrope, emulsifying, hydrotrope, and surfactant |
| Sodium Anisate | 0.5 | preservative |
| Isopropyl Palmitate | 5 | Light emollient with medium spreading properties and high refatting charasteristics. Good solubilizer for oil-soluble active ingredients. Shows very good wetting properties of hydrophobically coated pigments. |
| Polyquaternium-39 | 1 | Non-preserved polymer designed to reduce irritation from surfactants, provides silky skin feel and moisturization |
| Acetamide MEA | 2 | Humectant, skin conditioning agent |
| Neopentyl Glycol Diethylhexanoate | 5 | light moisturization in creams and lotions, excellent solvency, good slip, and is recommended for use in moisturizers for oily skin, non-volatile alternative to cyclomethicone. |
| Polyglyceryl-3 Beeswax | 2 | Inhibits oil syneresis, prevents ccrystallization, thockening and stabilizing agent |
| Carbomer | 1 | Gelling and thickening agent |
| NaOH | pH Adj | pH adjusting agent |
| Chlorphenesin | 0.5 | Preservative |
| Copper Gluconate | 0.5 | Antioxidant |
| *Eugenia Caryophyllata* (Clove) Bud Oil | 2 | Antiinflammatory |
| Water | q.s. to 100 | Diluent |

TABLE 13

Topical cream

| MATERIAL | % w/w | FUNCTIONALITY |
| --- | --- | --- |
| Olopatadine | 0.2, 0.7. or 1 | Active |
| Phenoxyethyl Caprylate | 3 | Emollient with excellent solvent properties for UV filters and lipophilic active ingredients |
| PEG-200 Hydrogenated Glyceryl Palmate | 2 | surfactant - solubilizing agent, cleansing, emulsifying, and solvent |
| Hydrogenated Polyisobutene | 5 | waterproofing agent and an emollient. An emollient helps to maintain the natural skin barrier, prevent moisture loss, and improve the texture of the skincare product |
| Triethoxycaprylylsilane | 2 | binding agent and emulsifier, slip agent |
| Cetearyl Ethylhexanoate | 3 | skin-conditioning agent, emollient |
| Neopentyl Glycol Diethylhexanoate | 3 | light moisturization in creams and lotions, It features excellent solvency, good slip, and is recommended for use in moisturizers for oily skin, non-volatile alternative to cyclomethicone. |

TABLE 13-continued

Topical cream

| MATERIAL | % w/w | FUNCTIONALITY |
|---|---|---|
| Phytosphingosine | 0.5 | crucial role in the skin barrier, |
| PEG-8 Dioleate | 2 | emulsifier, emollient, and lubricant. |
| Sorbitan Sesquioleate | 2 | nonionic low HLB value emulsifier |
| Oleth-20 | 1 | nonionic oil-in-water emulsifier and its nonionic nature makes it an ideal candidate for use in leave-on skin care products |
| Microcrystalline wax | 5 | viscosity agent, binder and emollient, |
| Xanthan Gum | 0.5 | binder , emulsion stabilizer , skin-conditioning agent - miscellaneous , surfactant - emulsifying agent |
| Cetyl Alcohol | 3 | emollient, emulsifier, thickener, and surfactant |
| Lanolin Alcohol | 2 | provide a smoother skin feel |
| Methyl Gluceth-20 | 5 | water soluble emollient and humectant |
| Sodium Acrylates Copolymer | 1 | binder, film former, viscosity increasing agent - aqueous, binding, film forming, opacifying, and viscosity controlling |
| Neopentyl Glycol Diethylhexanoate | 2 | Light emollient ester for slip, absorbency, and spreadability |
| Tocopherol | 0.5 | Antioxidant |
| Dehydroacetic acid | 0.5 | Preservative |
| Dimethylimidazolidinone Rice Starch | 2 | absorbent and viscosity controlling |
| Polydimethylsiloxane | 2 | serve as an anti-foaming agent, skin protectant and conditioner |
| Caffeine | 0.5 | reduce inflammation and puffiness |
| Water | q.s. to 100 | Diluent |

TABLE 14

Topical cream

| MATERIAL | % w/w | FUNCTIONALITY |
|---|---|---|
| Olopatadine | 0.2, 0.7. or 1 | Active |
| Povidone K30 | 4 | film former, emulsion stabilizer |
| Caprylyl Glycol | 3 | humectant |
| Bismuth Oxychloride | 0.5 | Texture Enhancer, Absorbent, pearlescent |
| Nylon 12 | 2 | absorbent and texture enhancer |
| Copper Tripeptide-1 | 0.3 | Antioxidant, stimulates collagen production |
| Myristyl Nicotinate | 0.5 | cell-communicating ingredient |
| Saccharide Isomerate | 5 | bursting with hydrating properties, and gives improved skin protection against dehydration and sensitivity with every use. |
| Squalane | 5 | moisturizing; oil-soluble antioxidant. |
| Caprylhydroxamic Acid | 0.5 | preservative |
| TALC | 1 | abrasive, absorbent, anticaking agent, bulking agent, opacifying agent, skin protectant; slip modifier, anticaking, bulking, opacifying, and skin protecting |
| Ethylbisiminomethylguaiacol Manganese Chloride | 0.5 | antioxidant |
| cetyl PEG/PPG-10/1-dimethicone | 0.5 | Texture Enhancer, Silicones |
| diisostearyl polyglyceryl-3 dimer dilinoleate | 4 | Skin-Softening, Emollients, Emulsifiers |
| Tween 80 | 3 | Nonionic surfactant high HLB |
| Span 80 | 2 | Nonionic surfactant low HLB |
| Stearyl Heptanoate | 4 | Emollient which melts at body temperature. Gives a silky, but non-oily skin feel. Especially suitable for skin care products |
| Bis-PEG/PPG-16/16 PEG/PPG-16/16 Dimethicone | 3 | skin-conditioning agent - occlusive, surfactant - emulsifying agent, emollient, emulsifying, skin conditioning, and surfactant |
| PEG 8000 | 5 | slip, softener and mold-release agent. It is a water-soluble carrier substance. It offers moisture-stabilizing effect in creams |

TABLE 14-continued

Topical cream

| MATERIAL | % w/w | FUNCTIONALITY |
|---|---|---|
| Petrolatum | 20 | moisturizer |
| panthenol | 0.5 | skin protectant with anti-inflammatory properties. It can help improve skin's hydration, elasticity, and smooth appearance. |
| Water | q.s. to 100 | Diluen |

TABLE 15

Topical cream

| MATERIAL | % w/w | FUNCTIONALITY |
|---|---|---|
| Olopatadine | 0.2, 0.7. or 1 | Active |
| Mineral oil | 10 | Emollient/Oil |
| White petrolatum | 15 | Emollient |
| Cetomacrogol 1000 | 6 | Emulsifier |
| Cetostearyl alcohol | 6 | Emulsifier |
| Polysrobate 80 | 8 | Surfactant |
| Glyceryl monostearate | 1 | Emulsifier |
| Xanthan gum | 0.3 | Viscosifying agent |
| Water | q.s. to 100 | Diluent |

TABLE 16

Topical Emollient cream

| MATERIAL | % w/w | FUNCTIONALITY |
|---|---|---|
| Olopatadine | 0.2, 0.7. or 1 | Active |
| Isopropyl myristate | 10 | Emollient/Oil |
| White petrolatum | 15 | Emollient |
| Ceteth-20 | 6 | Emulsifier |
| Ceteth-2 | 6 | Emulsifier |
| Polysrobate 80 | 8 | Surfactant |
| Glyceryl monostearate | 1 | Emulsifier |
| Stearic acid | 3 | Viscosifying agent |
| Emulsifying wax | 1 | Emulsifier |
| Bees wax | 3 | Bodifying agent |
| Water | q.s. to 100 | Diluent |

TABLE 17

Topical shampoo

| MATERIAL | % w/w | FUNCTIONALITY |
|---|---|---|
| Olopatadine | 0.2, 0.7. or 1 | Active |
| Caprylyl Glycol | 5 | Humectant |
| Propylene glycol | 5 | Humectant, solvent |
| beta Cyclodextrin | 1 | Solubilizing agent for olopatadine |
| C12-13 PARETH-23 | 1 | surfactant - cleansing agent, surfactant - solubilizing agent, emulsifying, and surfactant |
| C12-13 PARETH-3 | 2 | surfactant - emulsifying agent |
| Dimethicone | 5 | hair conditioning agent, skin-conditioning agent - emollient, solvent, emollient, hair conditioning, and skin conditioning |
| Trisodium Ethylenediamine Disuccinate | 0.5 | chelating agent |
| Sodium Lauroyl Sarcosinate | 1 | foaming agent and surfactant |
| Sodium Lauryl Sulfoacetate | 1 | surfactant (foaming agent) for both skin and hair. This mild plant-derived surfactant creates a rich, luxurious lather that effectively removes surface oil, dirt, and bacteria without stripping or drying sensitive skin or hair |
| Coco-Betaine | 1 | foam booster, natural surfactant |
| Glycol Distearate | 2 | creamy, pearlescent appearance to surfactant products without thickening them or negatively impacting lather |
| Dimethicone Crosspolymer | 1 | Texture Enhancer, Emollients, Silicones |
| Dimethiconol Panthenol | 3 | Hair conditioning agent |
| Methylchloroisothizolinone | 0.5 | preservative |
| Hydrogenated Starch Hydrolysate, | 2 | humectant (hydrator) and film-forming agent for added barrier protection in skin care products. |
| Caprylic/Capric Triglyceride | 5 | emollient, dispersing agent, solvent, antioxidant |
| Pentaerythrityl Tetra-Di-T-Butyl Hydroxyhydrocinnamate | 1 | stabilizer, antioxidant |
| Carbomer | 0.5 | Gelling agent, bbodifying agent |
| Isodecyl Neopentanoate | 2 | excellent emollient for sun care applications, soft skin feel, high spreadability, and high slip make |

TABLE 17-continued

Topical shampoo

| MATERIAL | % w/w | FUNCTIONALITY |
|---|---|---|
| Stearic acid | 2 | Thickening agent |
| PPG-3 Myristyl Ether | 2 | skin-conditioning agent and solvent |
| Hydrolyzed Wheat Protein | 0.5 | film former, hair conditioning agent, skin-conditioning agent - miscellaneous, antistatic, hair conditioning, and skin conditioning |
| POLYQUATERNIUM-7 | 1 | prevents or inhibits the buildup of static electricity and dries to form a thin coating that is absorbed onto the hair shaft. Polyquaternium-7 also helps hair hold its style by inhibiting the hair's ability to absorb moisture. |
| NaOH | pH adj | pH Adjusting Agent |
| Water | q.s. to 100 | Diluent |

TABLE 18

Topical shampoo

| MATERIAL | % w/w | FUNCTIONALITY |
|---|---|---|
| Olopatadine | 0.2, 0.7. or 1 | Active |
| Polyvinylpyrrolidone (PVP) | 2 | Antistatic, Binding, Emulsion stabilising, Film forming, Viscosity controlling, solubilizing agent |
| Polyviny alcohol (4%) | 5 | Surfactant, solubilizing agent |
| C12-15 Alkyl Benzoate | 5 | excellent solvent properties for lipophilic active ingredients |
| Bis-Aminopropyl Diglycol Dimaleate | 3 | restore damaged hair by repairing disulfide bonds broken |
| Dimethicone PEG-7 Isostearate | 1 | Hair conditioning |
| Guar Hydroxypropyltrimonium Chloride | 1 | antistatic agent, hair conditioning agent, viscosity increasing agent - aqueous, antistatic, film forming, skin conditioning, and viscosity controlling |
| Hydroxypropyl Cyclodextrin | 2 | chelating agent, emulsion stabilizer, masking, and skin conditioning |
| Phospholipids | 0.5 | controlling frizz, reversing dryness and damage, and leaving hair soft, shiny, and manageable. |
| sodium C12-14 olefin sulfonate, | 1 | surfactant - cleansing agent, cleansing, foaming, and surfactant |
| Amodimethicone | 3 | coats hair, providing great shine and conditioning to the hair. |
| Sodium Lauroyl Sarcosinate | 1 | foaming agent and surfactant |
| Sodium Cocoamphopropionate | 1 | surfactant, increase foaming capacity or stabilize foams, enhance the appearance and feel of hair, by increasing hair body, suppleness, or sheen, or by improving the texture of hair that has been damaged physically or by chemical treatment |
| Hexylene Glycol | 5 | Humectant |
| GMS Type II | 3 | Viscosifying agent, cosurfactant |
| Polysorbate 20, | 2 | Surfactant |
| Methylisothiazolinone | 0.5 | Preservative |
| Tetrasodium EDTA | 0.5 | Chelating agent |
| Sodium Chloride | 0.5 | thickener in shampoos and conditioners |
| Hydrolyzed Keratin, | 0.2 | hair conditioning agent, skin-conditioning agent - miscellaneous, antistatic, hair conditioning, and skin conditioning |
| Tocopherol | 0.2 | Antioxidant |
| Peg-4 Laurate | 1 | surfactant - emulsifying agent |
| Hypromellose | 1 | Thickening agent |
| Silicone Quaternium-8 | 1 | hair conditioning agent, antistatic, and hair conditioning |
| PEG-12 Dimethicone | 5 | hair conditioning agent, skin-conditioning agent - miscellaneous, hair conditioning, and skin conditioning |
| Water | q.s. to 100 | Diluent |

TABLE 19

Topical shampoo

| MATERIAL | % w/w | FUNCTIONALITY |
|---|---|---|
| Olopatadine | 0.2, 0.7. or 1 | Active |
| Polyvinyl alcohol (4% Z) | 2 | Surfactant, solubiliing agent |
| Glycerin | 5 | Humectant, Solvent |
| PEG 400 | 10 | Humectant, Solvent, viscosifying agent |
| Tyloxapol | 0.1 | Non-ionic surfactant |
| Ethylene Glycol Distearate | 1 | Pearlescing agent |
| Cetearyl Alcohol | 3 | Surfactant, viscosifying agent |
| Sodium Lauroyl Oat Amino Acids | 0.5 | anti-static, cosurfactants |
| Hydrogentated Castor Oil/Sebacic Acid Copolymer | 2 | Emollient, hair conditioning |
| Dimethyl Isosorbide | 5 | Solvent, Viscosity controlling |
| Pentaerythrityl Tetra-Di-T-Butyl Hydroxyhydrocinnamate | 0.5 | antioxidant, preservative |
| Stearic Acid | 3 | |
| PPPG-3 Benzyl Ether Myristate | 5 | Emollient, solvent |
| Dipropylene Glycol | 5 | Solvent, Viscosity controlling |
| 2-Oleamido-1,3-Octadecanediol | 5 | Emollient Skin conditioning |
| Arginine | 0.1 | conditioning and moisturizing agent |
| Aspartic Acid | 0.3 | hair conditioning agent |
| Zinc Picolinate | 1 | Soothing agent |
| Sodium Phytate | 1 | fine-bubble foam |
| Steareth-4 | 2 | Surfactant |
| Undeceth-5 | 2 | emulsifying, surfactant/cleansing |
| Undeceth-11 | 1 | emulsifying, surfactant/cleansing |
| Polyquaternium-7 | 2 | antistatic agent, film former, hair fixative, antistatic, and film forming |
| Polyquaternium-10 | 2 | antistatic agent, film former, hair fixative, antistatic, and film forming\ |
| Aloe Barbadensis Leaf Juice | 5 | Antiinflammatory, conditioning agent |
| Water | q.s. to 100 | Diluent |

TABLE 20

Topical shampoo

| MATERIAL | % w/w | FUNCTIONALITY |
|---|---|---|
| Olopatadine | 0.2, 0.7. or 1 | Active |
| Glycol Distearate | 1 | Pearlescing agent |
| Sodium Cocoyl Isethionate | 2 | surfactant |
| Disodium Laureth Sulfosuccinate | 2 | surfactant |
| Sodium Lauryl Sulfoacetate | 1 | surfactant (foaming agent) for both skin and hair. This mild plant-derived surfactant creates a rich, luxurious lather that effectively removes surface oil, dirt, and bacteria without stripping or drying sensitive skin or hair |
| Sodium Lauroyl Sarcosinate | 1 | improve the appearance of the hair (especially locks that are damaged) by boosting shine and body. |
| Propylene Carbonate | 5 | Solvent |
| Ethylhexyl Palmitate | 5 | Universal emollient with skin caring properties. Good solubilizing properties for active ingredients. |
| PPG-11 Stearyl Ether | 5 | Very high polar cosmetic emollient with a pleasant skin feel. Excellent solvent for lipophilic active ingredients and perfume oils. |
| GLYCERETH-26 | 1 | plasticizer (chemical added to resins and rubbers to make them more flexible), to bind ingredients together, a solvent, and softener. |
| PEG-55 Propylene Glycol Oleate | 5 | surfactant - cleansing agent, surfactant - solubilizing agent, and viscosity controlling |
| Magnesium Nitrate | 1 | hair conditioning |
| Phosphatidylcholine | 0.5 | Hair conditioning agent, surfactant |

TABLE 20-continued

Topical shampoo

| MATERIAL | % w/w | FUNCTIONALITY |
|---|---|---|
| Hydrolyzed Collagen | 0.1 | Antistatic, emollient, film forming agent, hair conditioner, humectant |
| Potassium Sorbate | 0.5 | preservative |
| Ppg-5-Ceteth-20 | 2 | emollient and surfactant |
| Laureth-2 | 5 | low HLB surfactant |
| Laureth-23 | 2 | high HLB surfactant |
| Stearyl Alcohol | 3 | Viscosifying agent |
| Hydroxypropyl Cellulose | 1 | Gelling agent and viscosifying agent |
| Stearamidopropyl Dimethylamine | 1 | Antistatic, Emulsifying agent, hair conditioner, surfactant |
| Phenylethyl Resorcinol | 0.5 | Antioxidant |
| Trisodium Ethylenediamine Disuccinate | 0.5 | Chelating Agent |
| Water | q.s. to 100 | Diluent |

TABLE 21

Topical shampoo

| MATERIAL | % w/w | FUNCTIONALITY |
|---|---|---|
| Olopatadine | 0.2, 0.7. or 1 | Active |
| Promulgen™ G | 3 | nonionic emulsifier |
| Hydroxypropyl Starch Phosphate, | 2 | Bulking, Viscosity controlling |
| Dipropylene Glycol | 5 | improve the texture and stability of the formulation; solvent; viscosity reducing agent |
| PEG/PPG-8/3 Laurate | 4 | solubilizer |
| Tween 20 | 3 | Surfactant |
| Span 20 | 5 | Surfacatant |
| Sodium Laureth Sulfate | 1 | surfactant |
| Sodium Lauryl Sulfate | 1 | Surfacatant |
| Cocamide MIPA | 2 | surfactant, viscosity increasing agent, emulsifier and stabilizer |
| NaCl | 1 | thickener in shampoos and conditioners |
| Sepigel 305 | 2 | Thickening agent |
| Carbomer | 0.5 | Gelling agent |
| 2-Oleamido-1,3-Octadecanediol | 2 | hair conditioning and skin conditioning agents; Used to increase the solubility of sparingly soluble substances in cosmetics |
| Methylisothiazolinone | 0.5 | preservative |
| Potassium Sorbate | 0.5 | preservative |
| PEG-150 Pentaerythrityl Tetrastearate | 2 | viscosity increasing agent - aqueous and emulsifying |
| PPG-2 Hydroxyethyl Cocamide | 2 | surfactant - emulsifying agent, surfactant - foam booster, viscosity increasing agent -aqueous, emulsifying, and surfactant |
| Sodium Lauroamphoacetate | 1 | hair conditioning agent, surfactant - cleansing agent, surfactant - foam booster, cleansing, foam boosting, foaming, hair conditioning, and surfactant |
| Laurdimonium Hydroxypropyl Hydrolyzed Keratin | 0.5 | Antistatic, hair conditioner |
| Trihydroxystearin | 1 | conditioning agent, a solvent and a viscosity-increasing agent, making this shampoo thicker and more spreadable |
| Xylitol | 2 | Humectant |
| Glycerin | 5 | Humectant |
| Laureth-5 Carboxylic Acid | 1 | surfactant |
| Water | q.s. to 100 | Diluent |

TABLE 22

Topical spray

| Material | % w/w | Functionality |
| --- | --- | --- |
| Olopatadine | 0.2, 0.7, or 1 | Active |
| Tyloxepol | 0.1 | Surfactant |
| Glycerin | 5 | Humectant |
| Isodecyl Neopentanoate | 3 | skin-conditioning agent - emollient, emollient, and skin conditioning |
| PEG/PPG-18/18 Dimethicone | 2 | surfactant - emulsifying agent and emulsifying, film forming agent |
| Glycyrrhiza Glabra Root Extract | 5 | soothing agent |
| SD Alcohol 40 (30%) | 45 | Srayability, reduce viscosity and surface tension |
| Disodium EDTA | 0.5 | Stabilizer |
| Water | q.s. to 100 | Diluent |

TABLE 23

Topical spray

| Material | % w/w | Functionality |
| --- | --- | --- |
| Olopatadine | 0.2, 0.7, or 1 | Active |
| Isopropyl Palmitate | 5 | Light emollient with medium spreading properties and high refatting charasteristics. Good solubilizer for oil-soluble active ingredients. Shows very good wetting properties of hydrophobically coated pigments. |
| Tween 80 | 5 | Surfactant |
| Acetyl Tetra Peptide-5 | 0.1 | Skin conditioning |
| Dicaprylyl Carbonate | 5 | skin-conditioning agent, emollient and solvent |
| Chlorphenesin | 0.5 | synthetic preservative |
| Propyl Gallate | 0.5 | antioxidant |
| EDTA | 0.2 | Chelating agent |
| Diisopropyl adipate | 5 | fragrance ingredient, plasticizer, skin-conditioning agent - emollient, solvent, |
| *Chamomilla Recutita* (Matricaria) Flower Extract | 5 | Anti-inflammation, moisturiser, skin repair |
| Isopropyl Alcohol | 30 | Sprayability, reduce viscosity and surface tension |
| Water | q.s. to 100 | Diluent |

TABLE 24

Topical spray

| Material | % w/w | Functionality |
| --- | --- | --- |
| Olopatadine | 0.2, 0.7, or 1 | Active |
| Ethylhexylglycerin | 0.5 | Hydroxyethyl Acrylate/Sodium Acryloyldimethyl Taurate Copolymer |
| Hexylene Glycol | 5 | Humectant, viscosity decreasing agent, solvent |
| Methyl Gluceth-20 | 5 | humectant, skin replenishing |
| Sodium hyaluronate | 0.1 | skin conditioning agent |
| Hydrolyzed Collagen | 0.1 | antioxidant, skin conditioning agent |
| SD Alcohol 40 (30%) | 40 | Sprayability, reduce viscosity and surface tension |
| Water | q.s. to 100 | Diluent |

TABLE 25

Topical spray

| Material | % w/w | Functionality |
|---|---|---|
| Olopatadine | 0.2, 0.7. or 1 | Active |
| Cyclopentasiloxane | 1 | improve the texture of formulations, helping products to glide on smoothly and evenly. It also has the added benefit of acting as a protective barrier to the skin, protecting the skin from moisture loss, allergens, and bacteria. |
| Cetyl dimethicone | 2 | antifoaming agent, skin-conditioning agent - occlusive, and emollient |
| Perfluorodecalin | 2 | Solvent |
| Phenoxyethyl Caprylate | 2 | Emollient with excellent solvent properties for lipophilic active ingredients |
| N-Hydroxysuccinimide | 0.5 | skin softening |
| Sodium Lactate | 0.5 | preservative, exfoliant, and humectant. |
| Sorbitan stearate | 1 | humectant to bind moisture, thicken the product, and stabilize the mixture of water and oils, emulsifier |
| Acetamide MEA | 2 | Humectant, skin conditioning agent |
| Dimethicone PEG-7 Isostearate | 3 | Emollient, skin conditioner, slip agent |
| PPG-20 Methyl Glucose Ether | 2 | water-soluble emollient and humectant |
| Choleth 24 | 0.5 | polyethylene glycol ether of cholesterol, reduces the surface tension of cosmetic ingredients which helps to form an emulsion |
| Sodium polyacrylate, | 0.5 | thickening agent, texture enhancer, film-forming agent, and emulsion stabilizer. |
| Hydroxyethyl cellulose | 0.05 | Film forming agent |
| Pentylene glycol | 3 | Humectant, solvent |
| PEG 400 | 5 | Humectant, solvent, viscosifying agent |
| Propylene glycol | 5 | Humectant, solvent, viscosifying agent |
| Isopropyl Alcohol | 30 | Sprayability, reduce viscosity and surface tension |
| Oleth-2 | 2 | low HLB value emulsifier |
| Oleth-20 | 0.6 | high HLB value emulsifier |
| Steareth 21 | 3 | high HLB value emulsifier |
| Water | q.s. to 100 | Diluent |

TABLE 26

Topical spray

| Material | % w/w | Functionality |
|---|---|---|
| Olopatadine | 0.2, 0.7. or 1 | Active |
| PEG/PPG-8/3 Laurate | 5 | solubilizer |
| Isopropyl Myristate | 5 | Universal cosmetic emollient with medium spreading properties. Low-viscous solvent for active ingredients. Shows very good wetting properties |
| PPG-3 Myristyl Ether | 2 | skin-conditioning agent and solvent |
| Palmitoyl Tetrapeptide-7 | 0.5 | regenerating peptide |
| Dimethicone PEG-7 Cocoate | 3 | impart the conditioning benefits of silicone to personal care products without contributing to greasiness or build-up that is normally associated with water-insoluble silicone fluids. |
| Hydrogenated Polyisobutene | 2 | waterproofing agent and an emollient. An emollient helps to maintain the natural skin barrier, prevent moisture loss, and improve the texture of the skincare product |
| PEG-7 Amodimethicone | 2 | skin-conditioning agent - emollient, humectant |
| 7-dehydrocholesterol | 0.5 | skin-conditioning agent - miscellaneous, viscosity increasing agent - nonaqueous, emulsion stabilising, |
| Propylene Glycol | 5 | Humectant, solvent |
| Caprylic/Capric Triglyceride | 10 | skin-conditioning agent - occlusive |
| Sorbitan Sesquioleate | 2 | low HLB surfactant |
| Polysorbate 20 | 5 | high HLB surfactant |

TABLE 26-continued

Topical spray

| Material | % w/w | Functionality |
| --- | --- | --- |
| Sodium Styrene/Acrylates/Divinylbenzene Copolymer, | 0.5 | opacifying agent, film forming |
| Cetearyl Alcohol | 0.5 | Film forming agent, viscosifying agent |
| Potassium Sorbate | 0.5 | Preservative |
| Sodium Metabisulfite | 0.5 | Preservative |
| SD Alcohol 40 | 30 | Spray ability, reduce viscosity and surface tension |
| Caprylyl Methicone | 5 | Solvent, surface tension lowering agent |
| Water | q.s. to 100 | Diluent |

TABLE 27

Topical ointment

| Material | % w/w | Functionality |
| --- | --- | --- |
| Olopatadine | 0.2, 0.7. or 1 | Active |
| C12-15 Alkyl Benzoate | 2 | skin-conditioning agent - emollient, antimicrobial, |
| Hexyl Laurate | 5 | skin conditioning emollient, solvent, and viscosity agent used to thicken beauty products and cosmetics |
| Propylene Glycol | 5 | Humectant, Solvent |
| Talc | 1 | Absorbent, Texture Enhancer, Opacifying gent |
| *Butyrospermum Parkii* (Shea) Butter | 15 | skin-conditioning agent - miscellaneous, skin-conditioning agent - occlusive, viscosityincreasing agent |
| Caprylic/Capric Triglyceride | 10 | fragrance ingredient and skin-conditioning agent - occlusive |
| Cyclopentasiloxane | 5 | skin-conditioning agent - emollient, solvent, |
| Dimethicone | 5 | antifoaming agent, skin-conditioning agent - occlusive, skin protectant |
| *Theobroma Cacao* (Cocoa) Seed Butter | 15 | fragrance ingredient, skin-conditioning agent - occlusive, skin protectant, emollient, |
| Diisopropyl Dimer Dilinoleate | 5 | skin-conditioning agent - emollient |
| Neopentyl Glycol Diethylhexanoate | 5 | skin-conditioning agent - emollient, viscosity increasing agent, Light emollient ester for slip, absorbency, and spreadability |
| Cetostearyl Alcohol | 5 | emulsion stabilizer, opacifying agent, surfactant - foam booster, viscosity increasingagent |
| Carnauba wax | 5 | Viscosity increasing agent |
| Mineral Oil | q.s. to 100 | Moisturizing agent |
| Sorbitan Monostearate | 5 | Low HLB Value Surfactant |
| Lecithin | 0.5 | Emollient, Esmulsifier |
| EDTA | 0.1 | Chelating agent |
| Alpha Tocopherol | 0.5 | Antioxidant |
| helichrysum italicum essential oil | 3.8 | anti-inflammatory, antioxidant, antimicrobial |
| Caprylhydroxamic Acid | 0.1 | Preservative |

TABLE 28

Topical ointment

| Material | % w/w | Functionality |
| --- | --- | --- |
| Olopatadine | 0.2, 0.7. or 1 | Active |
| Propylene carbonate | 5 | solvent, viscosity decreasing agent, and viscosity controlling |

TABLE 28-continued

Topical ointment

| Material | % w/w | Functionality |
| --- | --- | --- |
| Diisopropyl adipate | 10 | fragrance ingredient, plasticizer, skin-conditioning agent - emollient, |
| Cyclodextrin | 0.5 | Solubilizing agent |
| GMS Type II | 10 | skin-conditioning agent - emollient, surfactant |
| Isopropyl Isostearate | 5 | Elegant, medium emollient ester with low freeze point and excellent lubricity |
| Nylon-12. | 2 | Texture Enhancer, Absorbent |
| Glycol Stearate | 2 | Emollient, emulsifying agent, opacifying agent |
| Cetearyl Isononanoate | 5 | Cosmetic oil which forms a pleasant emollient film on the skin. Good solvent for active ingredients. Stable to oxidation. |
| EDTA | 0.5 | Chelating agent |
| Sodium PCA | 0.5 | Skin-Replenishing |
| Palmitoyl Oligopeptide | 0.2 | Skin-Restoring |
| Potassium Cetyl Phosphate | 1 | Surfactant, emulsifying agent |
| *Simmondsia Chinensis* (Jojoba) Seed Oil | 5 | skin-conditioning agent - occlusive, emollient, anti-inflammatory |
| Cetyl esters wax | q.s. to 100 | skin-conditioning agent - emollient, |
| Glycerin | 5 | Humectant, viscosifying agent |
| Methyl Gluceth-20 | 5 | Humectant, moisturizing agent |
| Caprylyl Glycol | 10 | humectant, help attract moisture to the skin, resulting in a smoother, softer complexion |
| Caprylic/Capric Triglycerides | 10.8 | skin-conditioning agent - occlusive |
| Span 80 | 5 | low HLB emulsifier |
| Tween 80 | 2 | high HLB emulsifier |
| Sorbitan Sesquioleate | 3 | low HLB emulsifier |
| Trisodium Ethylenediamine Disuccinate | 0.5 | Chelating agent |
| Dimethylmethoxy Chromanol | 0.5 | Antioxidant |
| Phenoxyethanol | 0.5 | Preservative/Antimicrobial |

TABLE 29

Topical ointment

| Material | % w/w | Functionality |
| --- | --- | --- |
| Olopatadine | 0.2, 0.7. or 1 | Active |
| PEG-200 Hydrogenated Glyceryl Palmate | 5 | surfactant - solubilizing agent, cleansing, emulsifying, and solvent |
| Ethylhexyl Palmitate | 10 | Universal emollient with skin caring properties. Good solubilizing properties for active ingredients. |
| PEG3350 | 30 | softener, slip, viscosifying agent |
| Simethicone/Dimethicone | 5 | Silicones, Slip Agents, antifoaming agent |
| PEG-20 Stearate | 3 | surfactant, emulsifying agent, solubilizing agent |
| PEG1450 | 11.3 | Wetting agent, viscosifying agent |
| PEG 400 | q.s. to 100 | Solvent, viscosifying agent, humectant |
| Aluminum starch octenyl succinate | 1 | Absorbent, anticaking agent, viscosity controlling agent |

TABLE 30

Topical ointment

| Material | % w/w | Functionality |
| --- | --- | --- |
| Olopatadine | 0.2, 0.7. or 1 | Active |
| PPG-11 Stearyl Ether | 10 | Very high polar cosmetic emollient with a pleasant skin feel. Excellent solvent for lipophilic active ingredients and perfume oils. |
| Di-C12-15 Alkyl Fumarate | 5 | skin-conditioning agent - emollient, emollient, and solvent |

TABLE 30-continued

Topical ointment

| Material | % w/w | Functionality |
| --- | --- | --- |
| C10-18 Triglycerides | 10 | skin-conditioning agent - occlusive, solvent, emollient, and skin conditioning |
| Polyglyceryl-6 Distearate | 5 | skin-conditioning agent - emollient, surfactant - emulsifying agent, |
| Bis-Diglyceryl Polyacyladipate-2 | 5 | skin-conditioning agent - emollient, |
| Castor Oil | 10 | Skin conditoning agent |
| Phospholipids | 0.5 | Emollient, Skin replenishing |
| Propylene Glycol Dicaprylate | 5 | skin-conditioning agent - occlusive and emollient |
| Bees wax | 5 | binder, emulsion stabilizer, epilating agent, fragrance ingredient, skin- conditioning agent, viscosity increasing agent |
| Emulsifying wax | 5 | stability, thickening agent |
| Span 80 | 3 | Low HLB Surfactant |
| Petrolatum | q.s. to 100 | Emollient |
| Mineral Oil | 13.1 | Moisturizing agent |
| Magnesium Ascorbyl Phosphate | 0.2 | Antioxidant |
| SODIUM METAPHOSPHATE | 0.5 | Chelating agent |
| Benzoic Acid | 0.2 | Preservative |

TABLE 31

Topical ointment

| Material | % w/w | Functionality |
| --- | --- | --- |
| Olopatadine | 0.2, 0.7. or 1 | Active |
| Isopropyl Palmitate | 10 | Light emollient with medium spreading properties and high refatting charasteristics. Good solubilizer for oil-soluble active ingredients. Shows very good wetting properties of hydrophobically coated pigments. |
| PPG-10 Methyl Glucose Ether | 5 | water-soluble emollient and humectant |
| Stearyl Alcohol | 8 | Emollient, emulsifying agent, opacifying, foam boosting agent |
| Cetyl alcohol, | 7 | Emollient, emulsifying agent, opacifying, foam boosting agent |
| Hexapeptide-9 | 0.2 | skin conditioning |
| Ceramide NP | 0.5 | Skin conditioning |
| Isostearyl Alcohol | 2.5 | Emollient, viscosity controlling agent, skin conditioner |
| Polymethyl Methacrylate | 0.5 | improve the skin's contour and reduce depressions in the skin due to scars, injury or lines |
| Sodium Hyaluronate | 0.2 | Humectant, skin conditioning agent |
| Bis-PEG/PPG-14/14 Dimethicone | 5 | skin-conditioning agent - emollient, surfactant |
| Caprylic/Capric Triglycerides | 10 | skin-conditioning agent - occlusive |
| Mineral Oil | 18.2 | Moisturizing agent |
| BHT | 0.2 | preservative |
| Diazolidinyl Urea | 0.2 | preservative |
| Squalane | 2 | Antioxidant |
| Sodium Gluconate | 1 | skin-conditioning agent, chelating agent |
| Aloevera Oil | 10 | moisturizing and emollient |
| Lecithin | 0.5 | Emollients, Skin-Replenishing |
| Oleth-2 | 3 | Low HLB Surfactant |
| Steareth-2 | 3 | Low HLB Surfactant |
| Steareth-21 | 2 | High HLB Surfactant |
| Water | q.s. to 100 | Diluent |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of acutely treating dermal pruritis in a human or animal consisting of topically administering to the skin a composition comprising 0.1 to 1% (w/w) olopatadine, wherein the dermal pruritis is caused by an insect bite, a dryness of the epidermis, a healing wound, an infection, a mechanical irritation, a burn, a synthetic chemical exposure, or a natural chemical exposure.

2. The method of claim 1 wherein the composition comprises 1% (w/w) olopatadine.

3. The method of claim 1 wherein the composition comprises 0.2 to 0.7% (w/w) olopatadine hydrochloride.

4. The method of claim 3 wherein the composition comprises 0.2% (w/w) olopatadine hydrochloride.

5. The method of claim 3 wherein the composition comprises 0.7% (w/w) olopatadine hydrochloride.

6. The method of claim 1 wherein the composition further comprises an ingredient selected from the group consisting of anti-inflammatory drugs, anti-microbial drugs, insecticides, and insect repellants.

7. The method of claim 1 wherein the composition is a solution packaged in a spray bottle.

8. The method of claim 1 wherein the composition is a solution packaged in a bottle containing a rollerball applicator.

9. The method of claim 1 wherein the composition is a gel, semi-solid or wax in a tube or container having a mechanism for advancing the composition to the tip of the tube or container.

10. The method of claim 1 wherein the composition is a gel, ointment or cream packaged in a squeezable container.

11. The method of claim 1 wherein the dermal pruritis is pruritis of the scalp and the composition is formulated as a shampoo.

12. The method of claim 1 wherein the composition is formulated within or on a surface of an erodible or non-erodible patch and the erodible or non-erodible patch is applied to the skin.

13. The method of claim 1 wherein the composition is formulated within or on a surface of a bandage and the bandage is applied to the skin.

* * * * *